US007538208B2

(12) United States Patent
Frey et al.

(10) Patent No.: US 7,538,208 B2
(45) Date of Patent: May 26, 2009

(54) **TYPE III SECRETION PATHWAY IN *AEROMONAS SALMONICIDA*, AND USES THEREFOR**

(75) Inventors: Joachim Frey, Bern (CH); Katja Stuber, Ittigen (CH); Julian C. Thornton, Victoria (CA); Michael A. Kuzyk, Richmond (CA); Jan Burian, Victoria (CA)

(73) Assignee: Universitat Bern, Bern (CH)

( * ) Notice: Subject to any disclaimer, the term of this patent is extended or adjusted under 35 U.S.C. 154(b) by 0 days.

(21) Appl. No.: 11/529,400

(22) Filed: Sep. 29, 2006

(65) Prior Publication Data

US 2009/0074817 A1 Mar. 19, 2009

Related U.S. Application Data

(60) Division of application No. 10/813,908, filed on Mar. 26, 2004, now Pat. No. 7,232,569, which is a continuation of application No. 10/416,902, filed as application No. PCT/CA01/01589 on Nov. 15, 2001, now abandoned.

(60) Provisional application No. 60/248,864, filed on Nov. 15, 2000.

(51) Int. Cl.
*C07H 21/04* (2006.01)
*C07H 21/02* (2006.01)
*A61K 49/00* (2006.01)
*A61K 39/00* (2006.01)
*A61K 39/38* (2006.01)

(52) U.S. Cl. .................... 536/23.7; 536/23.1; 424/9.1; 424/9.2; 424/184.1; 424/185.1; 424/190.31; 424/234.1; 424/246.1

(58) Field of Classification Search .................. 424/9.1, 424/9.2, 184.1, 185.1, 190.1, 234.1, 246.1; 530/300, 350; 536/23.1, 23.7
See application file for complete search history.

(56) References Cited

OTHER PUBLICATIONS

Ellis, A.E., "Immunization with bacterial antigens: furunculosis", Dev. Biol. Stand., vol. 90, pp. 107-116, 1997.*
Thornton, J.C., et al., "Novel antigens expressed by *Aeromonas salmonicida* grown in vivo", Infect. Immun., vol. 61, pp. 4582-4589, 1993.*
Karlyshev et al, *Gene*, 158:77-82 (1995).
Noonan et al, *Gene*, 175:127-131 (1996).
Yahr et al, *Journal of Bacteriology*, 179(22):7165-7168 (1997).
Yahr et al, Database Accession No. AF010150, XP002216597.

* cited by examiner

*Primary Examiner*—Rodney P. Swartz
(74) *Attorney, Agent, or Firm*—Womble Carlyle Sandridge & Rice PLLC

(57) ABSTRACT

Disclosed is a newly identified and characterized type III secretion system in *Aeromonas salmonicida*. The invention also encompasses the use of components of the novel secretion system in immunoprotection against *A. salmonicida* infection, as well as other diagnostic and therapeutic uses thereof.

8 Claims, 5 Drawing Sheets
(1 of 5 Drawing Sheet(s) Filed in Color)

TYPE III SECRETION PATHWAY IN *AEROMONAS SALMONICIDA*, AND USES THEREFOR

CROSS-REFERENCE TO RELATED APPLICATIONS

This application is a Divisional of U.S. application Ser. No. 10/813,908, filed Mar. 26, 2004 now U.S. Pat. No. 7,232,569; which is a Continuation of U.S. application Ser. No. 10/416, 902, filed Nov. 15, 2001 (now abandoned); which is a 371 of PCT/CA01/01589, filed Nov. 15, 2001; which claims priority under of 35 U.S.C. §119(e) of U.S. Provisional Application No. 60/248,864, filed Nov. 15, 2000; the entire disclosures of each of which are incorporated herein by reference.

FIELD OF THE INVENTION

This invention relates to bacterial secretion systems, and in particular to a newly identified and characterized type III secretion system in *Aeromonas salmonicida*. The invention also encompasses the use of components of the novel secretion system in immunoprotection against *A. salmonicida* infection, as well as other diagnostic and therapeutic uses thereof.

BACKGROUND OF THE INVENTION

Various publications are referenced throughout this publication, and full citations for each of these publications are provided at the end of the Detailed Description.

*Aeromonas salmonicida*, a Gram-negative, facultatively anaerobic, non-motile, rod shaped bacterium, growing at temperatures around 20° C., is the etiological agent of furunculosis in salmonids, causing most severe economic losses in production farms of salmon and trout. The disease is characterized in the sub-acute or chronic form by the presence of haemorrhagic necrotic lesions in the gills, gut and muscle, while in the acute form fish die apparently from toxaemia without showing particular external signs.

Due to the high contagiousity of the disease and the high mortality in salmon of all ages, particularly in the sea water growers, large amounts of antibiotics are used in closed and open waters for therapy of furunculoses (Munro and Hastings, 1993). Vaccination has become an important strategy to control furunculoses in fish farms (Ellis, 1997). However, the currently applied whole cell antigen vaccines seem to show considerable variability in efficacy, the origin of which remains currently unexplained (Thornton et al., 1993).

Knowledge of the mechanisms of pathogenicity of *A. salmonicida*, and in particular of the main virulence factors involved, is essential in the development of efficient strategies to prevent outbreaks of furunculoses caused by *A. salmonicida*. Currently, several potential virulence factors of *A. salmonicida* have been reported, including a surface-layer protein (Chu et al., 1991), the hemolysins ASH1, ASH3, ASH4 (Hirono and Aoki, 1993), salmolysin (Titball and Munn, 1985), the serine protease AspA (Whitby et al., 1992) and the glycerolipid-cholesterol acyltransferase (GCAT) (Lee and Ellis, 1990), but their role in pathogenesis is unclear and many of them seem not to play a primary role in virulence. This was demonstrated by *A. salmonicida* strains with deletion mutants of the GCAT and aspA genes which had no influence on virulence of the strains in inducing furunculoses.

SUMMARY OF THE INVENTION

A new ADP-ribosylating toxin named AexT (Aeromonas exoenzyme T) encoded by the gene aexT was identified in a virulent strain of *A. salmonicida*. *A. salmonicida* strains that were propagated for several passages on culture medium had lost expression of AexT, but still retained the aexT gene. AexT shows amino acid sequence similarity to the ADP-ribosyltransferase toxins ExoS and ExoT of *Pseudomonas aeruginosa* which are secreted by a type III-dependent secretion mechanism (Yahr et al., 1996). Regulation of aexT was shown to be dependent on contact with fish cells and could also be induced by $Ca^{2+}$ depletion of the medium. The aexT gene was found to be preceded by a consensus sequence for binding of a transcriptional activator known in *P. aeruginosa* as ExsA which is involved in type III mediated gene expression (Frank, 1997).

Based on these observations, we used broad range gene probes to identify in *A. salmonicida* a novel type III secretion system by means of the gene acrD (Aeromonas calcium response D) encoding a transmembrane spanning protein. The acrD gene has a high similarity to lcrD, a protein of the *Yersinia* sp. which is an inner membrane protein of the type III secretion apparatus in *Yersinia* sp. The acrD gene is flanked by further typical type III secretion genes which were designated acr1, acr2, acr3, acr4, acrD, acrR, acrG, acrV, and acrH, and which show significant similarity to pcr1, pcr2, pcr3, pcr4, pcrD, pcrR, pcrG, pcrV, and pcrH of *Pseudomonas aeruginosa* and to tyeA, sycN, yscX, yscY, lcrD, lcrR, lcrG, lcrV, and lcrH of *Yersinia enterocolitica*. All these genes play a predominant role in building up the type III secretion apparatus in the respective bacterium, including the regulation of the low calcium response (LCR) and chaperon functions. The genes isolated from *A. salmonicida* belong to the analogue of the virA operon, which is central in the type III secretion pathway of many Gram-negative pathogens of human, animals and plants (Fenselau et al., 1992; Gough et al., 1992; Michiels and Cornelis, 1991).

We have also determined that the type III secretion system in *A. salmonicida* is located on a 84 kb plasmid which is rapidly lost upon growth in culture medium. Biosynthesis of AcrV in *A. salmonicida*, the analogue to LcrV in *Yersinia*, requires as a trigger either low $Ca^{2+}$ conditions or contact with fish cells. Upon infection with *A. salmonicida* expressing AcrV, the cultured cells undergo significant morphological changes. Cultures derived from originally virulent *A. salmonicida* strains, which had lost the type III secretion genes including AcrV, lost virulence as they did not affect rainbow trout gonad cells morphologically after infection. Concomitantly to loss of the type III secretion genes, these cultures lost the expression of the aexT gene which specifies the ADP-ribosylating toxin of *A. salmonicida*.

Rainbow trout gonad cells infected with the virulent *A. salmonicida* and incubated in antiserum directed against recombinant AcrV-His protein could be protected from the toxic effect and showed only weak morphological changes. AcrV, which belongs to the type III secretion proteins is a determinative factor involved in virulence mechanisms of *A. salmonicida*, and is expected to provide new insights into basic mechanisms of pathogenicity of bacterial species. The components of the type III secretion system of *A. salmonicida* may be used as antigens for the development of sub-unit vaccines against infection of fish by *A. salmonicida*.

In one embodiment, the invention comprises an isolated 5.7 kb nucleic acid segment (SEQ ID NO:10) containing the type III secretion genes of *A. salmonicida*. In another embodiment, the invention comprises a nucleic acid segment that encodes protein having the amino acid sequence of SEQ ID NOS:1, 2, 3, 4, 5, 6, 7, 8, and 9, including variants that retain either biological activity or immunogenicity or both. Due to the degeneracy of the genetic code and the possible presence of flanking nucleic acid fragments outside of the coding regions, it will be understood that many different nucleic acid sequences may encode the amino acid sequence of SEQ ID NO NOS:1, 2, 3, 4, 5, 6, 7, 8, or 9, and variants, and that all such sequences would be encompassed within the scope of the present invention.

In a further embodiment, the invention relates to the use of AcrV as an immunogen, and to the use of AcrV in a recombinant or traditional vaccine to reduce the incidence of infection by *A. salmonicida.*

In another embodiment, the invention provides a means of diagnosing *A. salmonicida*, or other bacteria found to contain AcrV homologues, by the detection of the AcrV protein or the homologous proteins.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
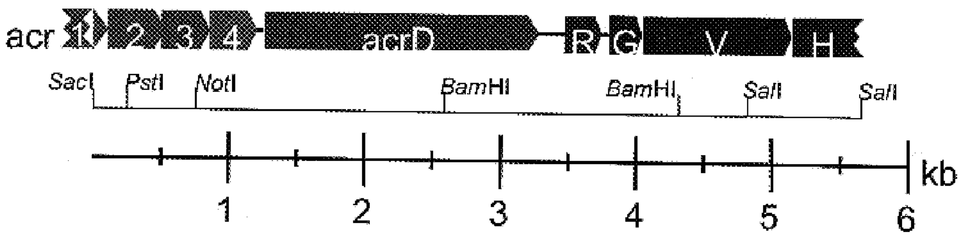
FIG. 1 is a genetic map of the type III secretion genes found in *A. salmonicida*. Boxes with arrowheads indicate open reading frames (ORFs). The size of the different genes (in kilobases) is shown by the scale bar. A restriction map containing restriction enzymes SacI, PstI, NotI, BamHI, and SalI is shown. Abbreviation used: acr, *Aeromonas* calcium response.

A 5.7 kb segment containing type III secretion genes of *A. salmonicida* that were cloned and sequenced correspond to the pcr locus (Pseudomonas calcium response) of *Pseudomonas aeruginosa* (Frank, 1997; Yahr et al., 1997b) and the virA operon and genes of the following operon of *Yersinia enterocolitica* (Cheng and Schneewind, 2000; Iriarte and Cornelis, 1999; Plano et al., 1991; Skrzypek and Straley, 1993; Motin et al., 1994; Price and Straley, 1989) and other Gram-negative animal and plant pathogens (Fenselau et al., 1992; Gough et al., 1992; Michiels and Cornelis, 1991). The most conserved gene at this locus was revealed to be the acrD gene encoding the AcrD protein, which showed 82% identical aa to the transmembrane spanning core proteins LcrD of the injectisome of the *Y. enterocolitica* type III secretion apparatus and PcrD of the injectisome of the *P. aeruginosa* type III secretion apparatus (Yahr et al., 1997b; Plano et al., 1991). Due to this high similarity, we conclude AcrD to have the analogous functions in the injectisome of the *A. salmonicida* type III secretion pathway.

The least conserved protein encoded on the cloned and analyzed segment is AcrV, which shows only 35% identical aa to PcrV of *P. aeruginosa* and 37% identity to LcrV of *Y. enterocolitica*. The main role of LcrV and PcrV, and accordingly also of AcrV, is assumed to be involved in sensing the bacterium-host interactions (Sawa et al., 1999; Bergman et al., 1991). We therefore interpret the significantly higher dissimilarity between AcrV and LcrV or PcrV, compared to the other gene products of the type III secretion locus (Table 3), to be due to the host specificity which seems to be determined by AcrV, LcrV or PcrV.

TABLE 3

*A. salmonicida* type III proteins compared to analogues in *P. aeruginosa* and *Y. enterocolitica*

| Protein in *A. salmonicida* | Analogue in *P. aeruginosa* | Similarity/ Identity[a)] | Genbank access. nr. | Analogue in *Y. enterocolitica* | Similarity/ Identity[a)] | Genbank access nr. | Proposed function |
|---|---|---|---|---|---|---|---|
| Acr1 | Pcr1 | 80/60 | AF010150 | TyeA | 83/69 | AF102990 | part of the translocation-control apparatus, required for selective translocation of Yops |
| Acr2 | Pcr2 | 63/44 | AF01050 | SycN | 77/62 | AF102990 | chaperone for YopN |
| Acr3 | Pcr3 | 62/47 | AF01050 | YscY | 69/54 | AF102990 | part of the type III secretion apparatus, secretion of Yop |
| Acr4 | Pcr4 | 66/55 | AF01050 | YscY | 64/52 | AF102990 | part of the type III secretion apparatus, secretion of Yop |
| AcrD | PcrD | 90/82 | AF01050 | LcrD | 90/82 | X67771 | inner memebrane spanning protein of type III secretion |
| AcrR | PcrR | 68/58 | AF01050 | LcrR | 71/58 | AF102990 | |
| AcrG | PcrG | 63/46 | AF010149 | LcrG | 64/42 | AF102990 | regulation of low calcium response |
| ArcV | PcrV | 50/35 | AF010149 | LcrV | 53/37 | X96797 | regulation of low calcium response, sensor suppression of TNFá and |

TABLE 3-continued

| A. salmonicida type III proteins compared to analogues in P. aeruginosa and Y. enterocolitica | | | | | | | |
|---|---|---|---|---|---|---|---|
| Protein in *A. salmonicida* | Analogue in *P. aeruginosa* | Similarity/ Identity[a)] | Genbank access. nr. | Analogue in *Y. enterocolitica* | Similarity/ Identity[a)] | Genbank access nr. | Proposed function |
| | | | | | | | interferon ã, protective antigen |
| AcrH | PcrH | 78/65 | AF010149 | LcrH (SycD) | 79/58 | AF102990 | Regulation of low calcium response, chaperon for YopD secretion |

[a)]given as % of similar/identical amino acids

Our analyses revealed the *A. salmonicida* type III secretion genes to be located on a plasmid of 84 kb. The plasmid was shown to be lost very easily in standard growth media, in particular after a slight raise in growth temperature. Concomitant to the loss of the type III genes in *A. salmonicida*, we detected the loss in virulence of the strain as measured by the infection of RTG-2 fish cell cultures, as well as the loss of production of ADP-ribosylating toxin aexT in supernatants and bacterial cell pellets of low $Ca^{2+}$ response induced *A. salmonicida* cultures. It is also noted that AexT biosynthesis induced by contact of *A. salmonicida* with RTG-2 fish cells disappeared in those strains or subcultures that had lost the type III secretion genes. Expression of the aexT gene must therefore be regulated by a mechanism which is dependent on type III secretion genes. In this context it must be noted that several genes of the type III secretion pathway of *Yersinia* spp., in particular LcrV, are down regulated and secretion and production of effector proteins is completely blocked in the presence of millimolar amounts of $Ca^{2+}$ (Forsberg et al., 1987). It also became apparent from tissue culture infection models that the absence of $Ca^{2+}$ in vitro mimics a yet undefined signal that is received by *Yersinia* species when they are adherent to eukaryotic cells and that induce both type III secretion genes and effector molecules such as YopE and Yops (Cornelis, 1998).

The dependence of aexT expression on type III secretion mechanism was also indicated by the presence of a consensus sequence upstream the aexT toxin gene in *A. salmonicida*, which shows full homology to the binding site of a transcriptional activator, known in *P. aeruginosa* as ExsA, which is involved in type III dependent gene expression (Frank, 1997). The expression of aexT in *A. salmonicida* is thus dependent on a functional type III secretion mechanism. The lack of production of AexT as detected in the type strain of *A. salmonicida* ATCC $33658^T$ as well as in the strain JF2397 which was derived from an originally virulent *A. salmonicida* strain, JF2267, in spite of the presence of a functional aexT gene, must therefore be due to the loss of the type III secretion pathway.

The AcrV protein of the novel type III secretion pathway of *A. salmonicida* plays an important role in pathogenesis by its role as a sensor and regulator of the system, as shown in other type III secretion systems. An important role in the secretion-related regulatory role in the low $Ca^{2+}$ response of *Y. pestis* is attributed to LcrV, which is localized to the bacterial surface and required for targeting of Yops of *Y. pestis* (Fields and Straley, 1999; Nilles et al., 1997). In addition, it was postulated that LcrV is also secreted by a special pathway which results its localization in the cytosol of infected cells but not the surrounding medium (Fields and Straley, 1999). Using a tissue cell model, it was shown that antiserum directed against LcrV prevented *Y. pestis* from injecting the Yop effector molecules into the host cells (Pettersson et al., 1999; Hueck, 1998). Active immunization of mice with recombinant LcrV antigen efficiently protected mice against challenge with *Y. pestis* (Leary et al., 1995). Our results showed that antibodies directed against recombinant AcrV, the analogous protein to LcrV, protected fish RTG-2 cells from damage caused by virulent *A. salmonicida* strain JF2267 and demonstrated that the AcrV plays an important role in type III secretion pathway mediated virulence of *A. salmonicida*.

The newly found type III secretion pathway plays a central role in pathogenicity of *A. salmonicida* via the secretion and direct injection of the ADP-ribosylating toxin AexT into the target cells. Loss of the type III secretion pathway, which is frequently observed, is due to the instability of a kb plasmid under culture conditions. Furthermore, loss of type III secretion genes such as acrD and acrV abolished expression of the aexT gene, and led to loss of virulence of *A. salmonicida*. As shown, surface exposed gene products of this type III secretion pathway, in particular AcrV, are potent candidates for new vaccines for the immune prophylaxis of fish against furunculosis.

The invention is further described by way of the following examples and results, which are not to be considered as limiting the scope of the invention. It will be appreciated by those skilled in the art, in light of this disclosure, that many changes can be made in the specific embodiments disclosed without departing from the scope of the invention.

EXAMPLES AND RESULTS

Materials and Methods

Bacterial Strains, Growth Conditions and Cloning Vectors:

*A. salmonicida* strains are listed in Table 1 below.

TABLE 1

| A. salmonicida used in this study and presence of acrD | | |
|---|---|---|
| Strain | origin | acrD[a)] |
| ATCC33658 | American Type Culture Collection, Type strain | – |
| JF2267 | Char (*Savelinus alpinus*), Switzerland | + |
| JF2397 | Laboratory strain, derivative of JF2267 | – |
| CC-23 | Salmon, Norway | + |
| CC-24 | Salmon, Norway | +/–[b)] |
| CC-27 | Salmon, Norway | + |
| CC-29 | Salmon, Scotland, UK | + |
| CC-30 | Salmon, Canada | + |
| CC-34 | Salmon, Canada | + |
| MT 44 | Spontaneous non virulent mutant | – |
| CC-63 | Salmon, Canada | + |
| CC-72 | Salmon, Canada | + |

[a)]As determined by Southern blot hybridization
[b)]Very weak hybridization signal indicating that only a minor part of the population of the culture contains the acrD gene

*A. salmonicida* type strain ATCC 33658$^T$ was purchased from the American Type Culture Collection. *A. salmonicida* strain JF2267 was freshly isolated from an arctic char (*Savelinus alpinus*) showing typical symptoms of furunculoses. *A. salmonicida* strain JF2397 was derived from strain JF2267 by repeated single colony isolations after each of nine passages propagated on LB agar medium at 22° C. for two days each passage. *A. salmonicida* strains were routinely cultured on blood agar plates (Trypticase soy agar supplemented with 0.1% $CaCl_2$ and 5% sheep blood) at 19° C. unless otherwise mentioned.

Liquid cultures of *A. salmonicida* were made by inoculation of Tripticase soy broth (TSB) (2.75 g/100 ml Tripticase soy broth without Dextrose (BBL® 11774, Becton Dickinson AG, Basle, Switzerland), 0.1% Glycerol, 0.1 M L-Glutamic acid pH 7.3) with fresh culture from solid medium and subsequent growth for 18 h at 19° C. For growth in $Ca^{2+}$-restricted medium, TSB was supplemented with 10 mM Nitrilotriacetic acid (Titriplex I, Merck 1.08416, Darmstadt, Germany).

For cloning and expression of cloned genes, *Escherichia coli* strains XL1-blue (recA1 endA1 gyrA96 thi-1 hsdR17 supE44 relA1 lac [F' proAB lacI$^q$Z$\Delta$M15 Tn10 (Tet$^T$)] (Bullock et al., 1987), and BL21 (DE3) (F' dcm ompT hsdS($r_B^-$ $m_B^-$) gal λ(DE3)) (Studier et al., 1990) respectively, were used. Plasmid pBluescriptII-SK$^-$ (Stratagene, La Jolla, Calif., USA), was used as basic cloning vector. For the construction of genes encoding poly-Histidine fusion proteins and their expression, plasmid pETHIS-1, a T7 promoter based expression vector (Schaller et al., 1999) was used. *E. coli* strains were grown at 37° C. in Luria-Bertani broth (LB) supplemented when necessary with ampicillin (50 μg/ml) for selection and maintenance of recombinant plasmids. When blue-white selection with pBluescriptIISK$^-$ was performed, 125 μM X-Gal medium was supplemented with 5-bromo-4-chloro-3-indolyl-β-D-thiogalacto-pyranoside.

Preparation of Genomic DNA, Cloning and Sequencing Procedures:

Genomic DNA of *A. salmonicida* was extracted by the guanidium hydrochloride method (Pitcher et al., 1989). A partial gene library of *A. salmonicida* JF2267 was constructed by cloning agarose gel purified SacI-SalI digested fragments of 4 to 6 kb size into vector pBluescriptII-SK$^-$ using standard procedures (Ausubel et al., 1999). Recombinant plasmids were screened by colony blot (Ausubel et al., 1999) using digoxigenin (DIG)-labeled DNA probes as described previously (Braun et al., 1999). Plasmids from *A. salmonicida* were purified using the method of Birnboim and Doly (Birnboim and Doly, 1979).

To construct a genomic library from *A. salmonicida* JF2267, 0.1 μg of DNA partially digested with Sau3a was ligated to ZapExpress BamHI prepared arms (Pharmacia, Uppsala, Sweden) and packed into phage Lambda. Two-hundred μl of freshly grown XL1-blue MRF' cells (Pharmacia) resuspended in 10 mM $MgSO_4$ were infected with the packed phages during 15 min at 37° C. Three ml of preheated (50° C.) Top Agarose (LB-broth containing 0.7% Agarose) supplemented with IPTG and X-Gal for blue/white selection were added and the mixture was poured onto an LB-Agar plate. Plates were incubated overnight at 37° C. and then used for screening of plaques. Positive plaques were cut out and stored overnight at 4° C. in 0.5 ml SM-buffer (100 mM NaCl, 8 mM $MgSO_4$, 50 mM Tris, pH 7.5, and 0.01% gelatine) containing 20 μl chloroform. 20 ml overnight cultures of XL1-blue MRF' grown in LB supplemented with 0.2% maltose and 10 mM $MgSO_4$ and 20 ml XLOLR cells (Pharmacia) grown in LB media were centrifuged for 5 min at 4,000 rpm and resuspended in 10 mM $MgSO_4$ to a final $OD_{600}$=1. Two-hundred μl the XL1-blue MRF' cells were added to 250 μl of the SM-buffer containing the positive phages and 1 μl ($10^7$ pfu) ExAssist™ helper phage. This mixture was incubated 15 min at 37° C. and 3 ml LB-broth were added and shaken another 3 hrs at 37° C. The cultures were then heated for 15 min at 70° C., centrifuged during 15 min at 5,700 rpm, 4° C., and the supernatant containing the pBK-CMV phagemid filamentous phage was decanted into fresh tubes. Two-hundred μl XLOLR cells were mixed with 100 μl supernatant and incubated for 15 min at 37° C., 300 μl LB-broth were added and the culture was incubated for another one hr at 37° C. Two-hundred μl of this culture were plated on LB-plates containing 50 mg/l kanamycin overnight at 37° C. Colonies were picked and mini-preps (using the QIAprep Spin Miniprep kit, Qiagen AG, Basle, Switzerland) performed for plasmid purification.

For sequencing, subclones of sequential DNA segments were generated with a double-stranded nested deletion kit (Pharmacia LKB, Biotechnology AB, Uppsala, Sweden). Sequencing was done with the dRhodamine Terminator Cycle Sequencing Kit (Applied Biosystems, Foster City, Calif., USA) according to the manufacturer's protocol using either T3 and T7 primers flanking the cloned inserts in pBluescriptII-SK$^-$ or customer-synthesized internal primers. All sequences were determined on both strands. Reaction products were analyzed on an ABI Prism 310 genetic analyzer (Applied Biosystems).

Sequence Data Analysis:

Sequence alignment and editing were performed by using the software Sequencher (Gene Codes Corporation, Ann Arbor, Mich., USA). Comparisons of DNA sequences and their deduced amino acid sequences with EMBL/GenBank and NBRF databases were performed using the programs BLASTN, BLASTX and BLASTP (Altschul et al., 1990). Potentially antigenic segments of AcrV were determined using the software ProtScale (Bairoch et al., 1995) and the software Coils output (Lupas et al., 1991). The molecular masses of the protein and its theoretical isoelectric pH (pI) were calculated by using ProtParam tool (Gill and von Hippel, 1989). Transmembrane prediction of the protein were made by using Tmpred (Hofmann and Stoffel, 1993).

PCR Amplification and Preparations of DIG-Labeled Gene Probes:

Template DNA was produced either by extraction of genomic DNA or by preparation of lysates from bacterial colonies. Lysates were obtained by resuspending five colonies of the corresponding bacterial cultures in 200 μl lysis buffer (100 mM Tris-HCl, pH 8.5, 0.05% Tween 20 (Merck), 0.24 mg/ml proteinase K (Roche Diagnostics, Rotkreuz, Switzerland) dissolved in pyrogen-free water, filtered through a 0.22 μm low protein binding membrane filter) followed by subsequent incubation for 60 min at 60° C. and 15 min at 97° C. Lysates were then cooled on ice and used as PCR templates.

PCR amplifications were performed with either a PE9600 or PE2400 automated thermocycler with MicroAmp tubes (Applied Biosystems). The reaction was carried out in a 50 μl reaction mix (10 mM Tris-HCl, pH 8.3, 1.5 mM $MgCl_2$, 50 mM KCl, 0.005% Tween 20, 0.005% NP-40 detergent, 170 μM of each deoxinucleoside triphosphate (dATP, dCTP, dGTP, dTTP), 0.25 μM of each primer, 2.5 units Taq DNA polymerase (Roche Diagnostics)), and 100 ng of template DNA or 5 μl lysate. For the production of DIG-labeled probes, PCR mixtures were supplemented with 40 μM digoxigenin- 11-dUTP (Roche Diagnostics). PCR conditions were as follows: 3 min at 94° C. followed by 35 cycles of 30 s at 94° C., 1 min at the corresponding annealing temperature (Table 2), and 30 s at 72° C.

TABLE 2

Oligonucleotide primers

| Name | Sequence[a] 5' to 3' | Residue Nos. of SEQ ID NO:10[b] | Annealing Temp ° C. |
|---|---|---|---|
| AslcrD-L[c] | GCCCGTTTTGCCTATC-AA | 1159-1176 | 60 |
| AslcrD-R[c] | GCGCCGATATCGGTAC-CC | 2028-2011 | 60 |
| AcrV-L[c] | TTCGTCGGCTGGCTTG-ATGT | 4144-4163 | 58 |
| AcrV-R[c] | GAACTCGCCCCCTTCC-ATAA | 4734-4715 | 58 |
| AsacrVt-L[d] | gggaattcGATGAGCA-CAATCCCTGACTAC (SEQ ID NO:11) | 4104-4125 | 57 |
| AsacrVt-R[d] | atgcggccgcAAATTG-CGCCAAGAATGTCG (SEQ ID NO:12) | 5188-5169 | 57 |
| AsacrVN'-R[d] | tcgcggccgcACCCTT-TACGCTGATTGTC (SEQ ID NO:13) | 4555-4537 | 57 |
| AsacrVC'-L[d] | cggaattcGTTGCGGG-ATGAGCTGGCAG (SEQ ID NO:14) | 4554-4573 | 57 |
| AsacrVC'-R[d] | tcgcggccgcACTCGG-CTTCTATGCCACTC (SEQ ID NO:15) | 4987-4968 | 57 |

[a]Lowercase letters indicate nucleotides added to create restriction enzyme recognition sites (underlined) for cloning.
[b]Based on nucleotide sequence of *A. salmonicida* JF2267
[c]Primer used for gene probe preparation
[d]Primer used for amplification of gene acrV, acrV-N, and acrV-C respectively In addition, an extension step of 7 min at 72° C. was added at the end of the last cycle in order to ensure fall length synthesis of the fragments.

Curing of Type III Secretion Genes from *A. salmonicida:*

In order to study the segregation of the type III secretion genes in *A. salmonicida* strain JF2267, the strain was inoculated in LB-broth at a density of $A_{600}$=0.08 and incubated 2½ hrs at 19° C. Then the culture was split in two. One part was kept for continued growth at 19° C., while the other part was incubated at 22° C. Samples were taken at different time points from both cultures and spread on LB-agar medium. The plates were then incubated at 19° C. for 24 hrs. Subsequently, colony blot hybridizations were performed using gene probes to determine the loss of specific genes.

Pulsed-Field Gel Electrophoresis (PFGE):

The bacterial strains *A. salmonicida* JF 2267 and JF2397 were grown on LB agar for one day at room temperature. Then bacterial suspensions in 10 mM Tris, 10 mM EDTA, pH 8.0, sterile, were prepared to a final $OD_{600}$ of 5. Three-hundred μl of 1.5% Sea Kem gold agarose (FMC Bioproducts, Maine, USA) in 100 mM Tris, 100 mM EDTA, pH 8.0, was added to 300 μl of bacterial cell suspension. Plugs were immediately poured in sterile moulds and kept on ice until hardened. The plugs were then incubated at 50° C. overnight in sterile 1.5 ml 0.5 M EDTA, 1% N-lauroylsarcosin, 2 mg/ml proteinase K (Roche Diagnostics), pH 8.0, by shaking. The next day, the plugs were thoroughly washed 5 times over the whole day at room temperature in sterile TE buffer (10 mM Tris, 1 mM EDTA, pH 8.0) and stored in sterile 0.5 M EDTA, pH 8.0, at 4° C. until further use. To digest the plugs they were first incubated in 4× Buffer H (Roche Diagnostics) for 10 min at 22° C. Then the plugs were incubated at 37° C. by shaking for 7½ hrs in 2× Buffer H containing 40 U of NotI (Roche Diagnostics). They were then placed into the slots of a 1% Sea Kem gold agarose gel in 0.5×TBE and sealed with 1% Sea Kem gold agarose. The gel was then equilibrated in 0.5×TBE at 12° C. using an Electrophoresis CHEF-DR® III system (BioRad Laboratories, Hercules, Calif., USA). To separate NotI DNA fragments, the field was 6V/cm, having an angle of 120°, starting with 1 s and ending with 12 s. The duration of the PFGE was 14 hrs and it was performed at 12° C. The gel was stained 30 min at room temperature in water containing 0.5 μg/ml ethidium bromide, washed two times with water and analyzed under a UV-light. Additionally, the gel was further used for Southern-blotting.

Southern-Blot Analysis:

Southern-blotting was done by alkaline transfer onto positively charged nylon membranes (Roche Diagnostics) with an LKB 2016 VacuGene vacuum blotting pump (Pharmacia LKB). To depurinate the agarose gels they were incubated for 10 min in 0.25 M HCl, and subsequent transfer was performed with 0.4 M NaOH for 1½ hrs. After blotting, membranes were baked for 30 min at 80° C. under vacuum. After at least one hr of prehybridization, hybridization was carried out in 5×SSC (1×SSC in 0.15 M NaCl plus 0.015 M sodium citrate)-1% blocking reagent (Roche Diagnostics)-0.1% N-lauroylsarcosine sodium salt-0.02% sodium dodecyl sulphate (SDS) at 68° C. overnight, using DIG-labeled DNA as probe. Membranes were washed under nonstringent conditions twice for 5 min each with 50 ml of 2×SSC-0.1% SDS per 100 $cm^2$ at 22° C., followed by medium-high-stringency washing twice for 15 min each with 50 ml of 0.2×SSC-0.1% SDS per 100 $cm^2$ at 68° C. The membranes were then processed with phosphatase-labeled anti-DIG antibody (Roche Diagnostics) according to the manufacturer's protocol. Signals were produced with chemiluminescent substrate (CSPD, Roche Diagnostics).

Pulsed-field gels were treated for Southern-blotting by using the same solutions as described above. To depurinate the agarose gels efficiently, they were incubated for 20 min in 0.25 M HCl, and then equilibrated for 20 min in 0.4 M NaOH. Transfer was performed for 3 hrs and the gels were treated as described above.

Expression of Purification of His-Tailed Fusion Protein AcrV:

Oligonucleotide primers used to amplify the whole acrV gene are given in Table 2. The PCR reactions were carried out as described above with the exception of using Pwo DNA polymerase (Expand Long Template PCR System kit, Roche Diagnostics) instead of Taq DNA polymerase and genomic DNA of *A. salmonicida* JF2267. The PCR products were purified by using the High Pure™ PCR Product Purification Kit (Roche Diagnostics) as described by the manufacturer's protocol. Then the acrV PCR product was cloned into pGEM-T vector (Promega, Madison, Wis., USA), having 3'-T overhangs at the insertion sites, as described in the manufacturer's protocol and transformed into *E. coli* strains XL-1 Blue. The resulting plasmid was designated pJFFIVB873. The cloning of the PCR products into pGEM-T vector was used to provide efficient restriction of the subcloned fragments. Plasmid pJFFIVB873 was then digested with EcoRI and NotI, and the DNA fragment was inserted into the T7-promoter-based expression vector pETHIS-1 (Schaller et al., 1999). The resulting plasmid, pJFFETHISacrV4 was purified and controlled by DNA sequencing to assure the fusions with the vector's poly-His codons and then transformed into *Escherichia coli* BL21 (DE3) cells (Novagen) for expression. Expression was induced by addition of 1 mM IPTG to cultures and incubation continued for another 3 h. The cells were sedimented by centrifugation at 3000×g for 10 min, resuspended in 5 ml PN buffer (50 mM $NaH_2PO_4$, pH 8.0, 300 mM NaCl), sonicated with a microtip for 4 min with the power output control at 1 and a duty cycle of 50% (1 s pulses) in a Branson Sonifier 250 (Branson Ultrasonics, Danbury, Conn., USA). Then guanidine hydrochloride was added to a final concentration of 6 M and was incubated overnight at 4° C. on a shaker. The mixture was loaded onto a prewashed 2.5 ml bed volume $Ni^{2+}$ chelation chromatography column (Qiagen) and washed once more with 30 ml PNG buffer (50 mM $NaH_2PO_4$, pH 8.0, 300 mM NaCl, 6 M guanidine hydrochloride). Step elutions of the proteins were performed by adding 10 ml PNG buffer at each different pH (7.0, 6.0, 5.5, 5.0, and 4.5) and fractions of 1 ml were collected. The fractions were dialyzed and analyzed on 15% PAGE. The purified fusion proteins were eluted at pH 4.5.

Production of Monospecific Rabbit Anti-AcrV Antibodies and Immunoblot Analysis:

Monospecific, polyclonal antibodies directed against AcrV were obtained by immunizing rabbits subcutaneous with 80 µg of recombinant polyhistidine-tailed AcrV protein in 200 µl PN buffer and 150 µl NaCl (0.85%) mixed with 350 µl Freund's complete adjuvant (Difco Laboratories, Detroit, Mich., USA) followed by a booster immunization with the same amount of protein in Freund's incomplete adjuvant (Difco) 3 weeks later. The animals were bled 22 d after the booster immunization according to standard protocols (Harlow and Lane, 1988).

Infection of Fish Cell Cultures with *A. salmonicida*:

Rainbow trout (*Oncorhynchus mykiss*) gonad cells (RTG-2, ATCC CCL-55) were grown in 75 $cm^2$ tissue culture flasks (Techno plastic products AG, Trasadingen, Switzerland) at 22° C. in minimum essential medium (GibcoBRL Life Technologies, Basel, Switzerland) supplemented with 2 mM L-glutamine (GibcoBRL), 1× non-essential amino acids (GibcoBRL), 3 g/l sodium bicarbonate and 10% foetal bovine serum. Three days before infection the cells were trypsinized and 4 mio cells were seeded into a 25 $cm^2$ tissue culture flask. Monolayered RTG-2 cells were infected with *A. salmonicida* cells resuspended in phosphate buffered saline (PBS) pH 7.4 at a multiplicity of infection of 20:1 or 2:1 (bacteria/fish cells). As a control also 100 µl of pure PBS pH 7.4 were added to cultured fish cells. After 24 hrs of infection at 15° C. the fish cells were photographed under a green filtered phase contrast microscope (Aixovert 100, Zeiss, Jena, Germany). To detach the cultured cells from the flask, the flask was shaken by hand. The suspended cells were centrifuged for 5 min at 4,000 rpm. Lysis of the fish cells was performed in 100 µl distilled water with two subsequent freeze thawing steps and verified by microscopy. The lysed fish cells were used for further analyzes on Western-blots.

Protection Assay Using Rabbit Antiserum AcrV:

RTG-2 fish cells were grown as described above. Two days before infection 20 million of trypsinized RTG-2 fish cells were seeded into 24 well culture plates (1.9 $cm^2$) (Techno plastic products AG, Trasadingen, Switzerland). Rabbit antiserum directed against AcrV as well as control preserum were decomplemented for 30 min at 56° C. A fresh culture of *A. salmonicida* (at end exponential growth phase) was washed and resuspended in PBS pH 7.4 and mixed with either preserum or anti AcrV antiserum at a ratio of 1:1, 1:10, 1:100, 1:1000 or 1:10,000. Bacteria were incubated with the serum at 18° C. for 30 min. The opsonized bacteria were added to the fish cells in a ratio of 20:1 or 2:1 (bacteria/fish cells). After 21 hrs of infection at 15° C. the fish cells were photographed as described before and inspected for morphological changes.

SDS-PAGE and Immunoblot Analysis:

Proteins were separated by polyacrylamide gel electrophoresis (SDS-PAGE) as described by Laemmli (Laemmli, 1970) using 15% or 10% polyacrid gels and transferred to a nitrocellulose membrane (BioRad Laboratories). For immunoblotting, Western-blots were blocked with 1% milk buffer for at least one hour and then incubated with the rabbit antiserum AcrV (1:2000) or with the rabbit preserum (1:1000) in milk buffer overnight at 4° C. The membranes were then washed thoroughly with water before phosphatase-labelled conjugate (Goat anti-Rabbit IgG (H+L) [cat. no. 075-1506], Kirkegaard & Perry, Gaithersburg, Md., USA) diluted 1:2000 in milk buffer was added. The reaction was visualized 90 min later by incubation with BCIP-NBT (Ausubel et al., 1999).

Cloning and Sequence Analysis of the virA Locus a Type III Pathway of *A. salmonicida*:

Analysis of *A. salmonicida* strain JF2267 with an array of broad range probes for detection of type III secretion pathways revealed a strong signal with the lcrD subset of the probes, indicating the presence of a new type III secretion pathway. Subsequent Southern-blot analyses showed a 4.8 kb fragment of SacI-SalI digested genomic DNA of strain JF2267 reacting with the lcrD probe. This fragment was cloned on vector pBluescriptII-SK⁻ leading to plasmid pJFFIVB638 which was subsequently sequenced. DNA sequence analyses revealed the presence of eight open reading frames (ORF) (FIG. 1) which showed strong similarity to the genes encoded on the virA operon of the type III secretion pathway of *Yersinia pestis* and *Pseudomonas aeruginosa*. In analogy to the *Y. pestis* genes, we named them acr1, acr2, acr3, acr4, and acrD (Aeromonas calcium response (FIG. 1)). They are located on a single operon followed by a transcription termination signal similar to the virA operon of *Y. pestis*, *Y. enterocolitica* and *Pseudomonas aeruginosa* (Boland et al., 1996; Iriarte and Cornelis, 1999; Plano et al., 1991; Cornelis, 1998; Yahr et al., 1997a). The similarities of the genes acr1, acr2, acr3, acr4 and acrD with the analogues in *Y. enteroclitica* and in *P. aeruginosa* are given in Table 2. Downstream lcrD we identified a locus with a canonical promoter sequence followed by further genes named acrR, acrG, and acrV on a separate operon (FIG. 1) according to the corresponding genes in *Y. pestis* (Table 3) (Barve and Straley, 1990; Skrzypek and Straley, 1993; Nilles et al., 1998). The ORF of the putative acrV gene seemed to be incomplete on the 4.8 kb SacI-SalI fragment of pJFFIVB638, and represented only the 5'-half of the gene. The remaining part of acrV and part of acrH located downstream of acrV were cloned separately from the λ phage gene library of *A. salmonicida* as an overlapping clone which was obtained by screening the gene library using a gene probe for the 5'-half of acrV which was produced by PCR with primers AcrV-L and AcrV-R (Table 2). The resulting plasmid based on vector PBK-CMV was designated pJFFIVB832. From this plasmid, a 0.9 kb SalI fragment containing the 3' end of acrV and part of the downstream gene acrH was subcloned on pBluescriptII-SK and designated pJFFIVB828.

Figure 2:
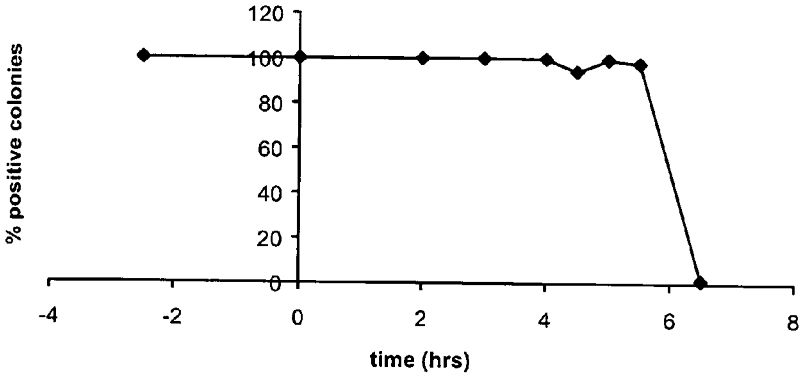
FIG. 2 is a segregation curve of *A. salmonicida* JF2267. An *A. salmonicida* JF2267 LB-culture was first incubated 2% hrs at 19° C. and then at 22° C. for 7 hrs. Colony-blotting was performed to analyze the LB-culture at 10 different time points for positive, respectively negative colonies.
Figure 3:
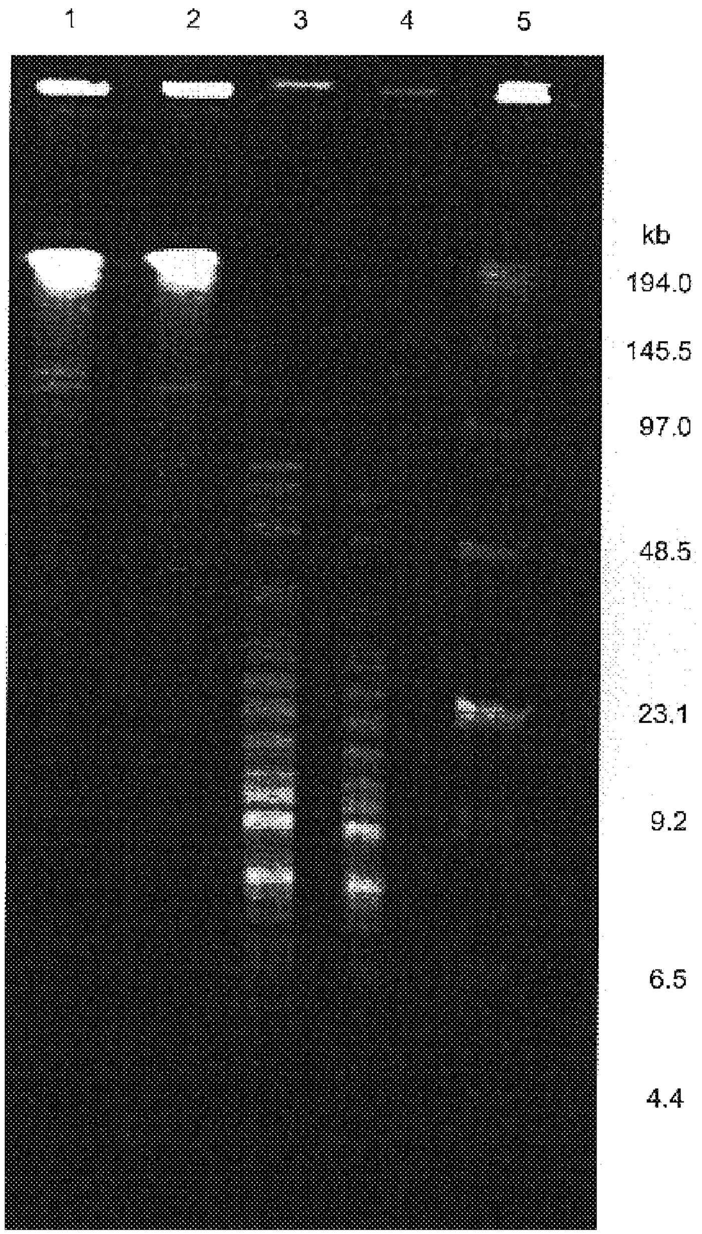
FIG. 3 shows a pulsed-field gel electrophoresis of *A. salmonicida* strain JF2267, and strain JF2397. (Lane 1) JF2267, undigested. (Lane 2) JF2397, undigested. (Lane 3) JF2267 digested with NotI. (Lane 4) JF2397 digested with NotI. (Lane 5) Low Range PFG Marker (New England Biolabs). The white arrows indicate the bands that hybridized on Southern blots with the acrD gene probe.

Instability of the Genes Belonging to the Type III Pathway in *A. salmonicida*:

When we analyzed the different *A. salmonicida* strains with a specific probe for acrD, we discovered by using Southern blot hybridization that the acrD gene was present only in strain JF2267 but not in the derivative strain JF2397 which had undergone nine passages of subsequent single colony cloning isolation. Additionally, the type strain of *A. salmonicida*, ATCC 33658$^T$, did not show a signal with the acrD probe. However, several *A. salmonicida* strains that were freshly isolated from salmon and trout with furunculoses did contain acrD (Table 1). These results indicate that the type III secretion pathway of *A. salmonicida* may be lost easily. In order to get an estimate on the loss of the type III secretion genes, we have analyzed the kinetics of disappearance of acrD after a shift of growth temperature of strain JF2267 from 19° C. to 22° C. Colony hybridization with the acrV probe revealed that in a fresh culture of strain JF2267, the acrD gene was present in all cells grown at 19° C. After the shift to 22° C., acrD was still present for further 5½ hrs, following which it was lost very rapidly within less than 1 hr (FIG. 2). Taking into account the generation time of 2 h for *A. salmonicida* under the given growth conditions, the acrD gene was lost within two generations. To analyze the loss of acrD further, undigested and NotI digested genomic DNA of *A. salmonicida* strain JF2267 and of the acrD deficient derivative strain JF2397 were submitted to pulse field gel electrophoresis (PFGE) and subsequent Southern blot hybridization with the acrD probe. PFGE analyses of total undigested DNA revealed the presence of two large plasmids in strain JF2267 while in strain JF2397 only one of the two plasmids was seen (FIG. 3). Digestion of the total DNA from these two strains with the rarely cutting enzyme NotI revealed the lack of a 84 kb band in strain JF2397 compared to JF2267 as the sole detectable difference (FIG. 3). Southern-blot hybridization of the DNA on this gels with the acrD probe confirmed the larger plasmid and the 84 kb NotI fragment of strain JF2267 to contain acrD gene. Neither the remaining large plasmid in JF2397 nor any of its NotI fragments hybridized with the AcrV probe. This indicates that the type III secretion genes, or at least the virA operon thereof, are located on a large plasmid in the size range of 84 kb.

Presence of arcD in *A. salmonicida* Strains:

In order to assess the presence of the acrD gene in various *A. salmonicida* strains, DNA samples extracted from *A. salmonicida* Type strain ATCC33658 and various field strains isolated from salmon or char were digested with restriction enzymes SalI and SacI, separated by 0.7% agarose gel electrophoresis, blotted onto nylon membranes and hybridized with the acrD gene probe. The Southern blot revealed the presense of the acrD gene on a 4.8 kb fragment in all strains except in the type strain ATCC33658, the laboratory strain JF2396 which was used for the type III secretion genes, and *A. salmonicida* strain MT44 known to be a virulent for trout. One field strain, #24, showed a very weak hybridization signal indicating that the culture contains acrD only in a minor population of the cells (Table 1).

Figure 4:
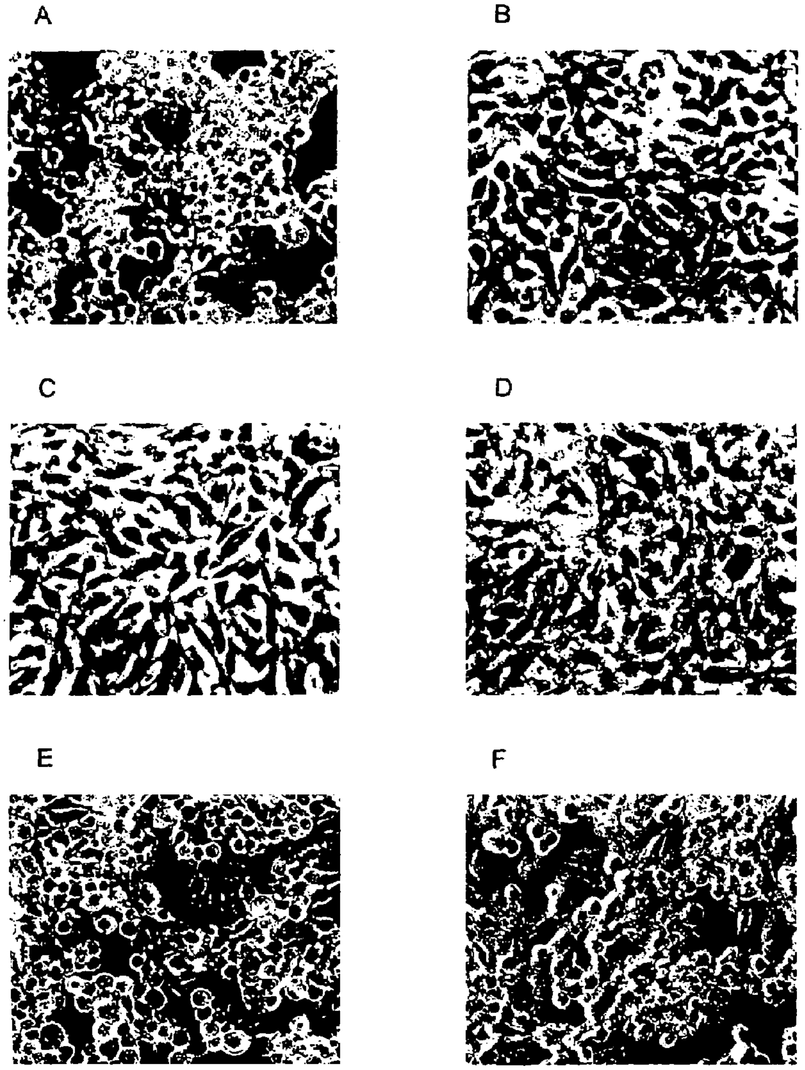
FIG. 4 shows infection of fish cells with *A. salmonicida* ATCC 33658$^T$, JF2267, and JF2397. RTG-2 cells infected with JF2267 (A), ATCC 33658$^T$ (B), JF2397 (C), and pure PBS (D). RTG-2 cells infected with JF2267 and monospecific polyclonal antibodies against AcrV were protected (E), whereas RTG-2 cells infected with JF2267 and anti-AcrV preserum were not. Pictures were taken 24 hrs after infection, respectively 21 hrs after the protection assay under a phase contrast microscope.

Infection of RTG-2 Fish Cells and Protection of Cell Damage with anti-ArcV Antiserum:

Freshly cultured *A. salmonicida* strain JF2267 was used to infect RTG-2 cells. After 24 hrs of incubation the fish cells were rounded up and also detached from the plastic support (FIG. 4A). In contrast cells infected with *A. salmonicida* type strain ATCC 33658$^T$ or strain JF2397 (FIGS. 4B and C), both known to be devoid of acrD and acrV, showed no morphological changes at all in spite of a massive multiplication of the bacteria in the cultures. RTG-2 fish cells which were incubated with PBS buffer as control showed no morphological changes like the cells infected with the acrD and acrV deficient strains JF2397 or ATCC 33658$^T$ (FIG. 4D).

In order to assess the presence of the acrD gene in various *A. salmonicida* strains, DNA samples extracted from *A. salmonicida* Type strain ATCC 33658 and various field strains isolated from salmon or char were digested with restriction enzymes SalI and SacI, separated by 0.7% agarose gel electrophoresis, blotted onto nylon membranes and hybridized with the acrD gene probe. The Southern blot revealed the presense of the acrD gene on a 4.8 kb fragment in all strains except in the type strain ATCC 33658, the laboratory strain JF2397 which was used for the type III secretion genes, and *A. salmonicida* strain MT44 known to be a virulent for trout. One field strain, #24, showed a very weak hybridization signal indicating that the culture contains acrD only in a minor population of the cells (Table 1).

Expression of AcrV in *A. salmonicida:*

Figure 5:
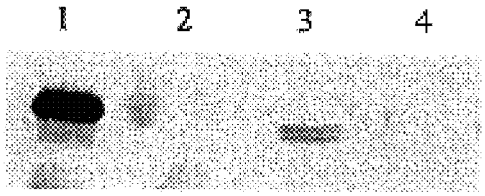
FIG. 5 shows low $Ca^{2+}$ response induced AcrV expression in *A. salmonicida* JF2267. The picture shows an immunoblot reacted with specific rabbit anti-AcrV antiserum. Strains ATCC 33658$^T$ (lane 2), JF2267 (lane 3) and JF2397 (lane 4) were grown in $Ca^{2+}$ depleted medium, harvested by centrifugation and analyzed on 15% SDS PAGE followed by immunoblotting. Lane 1 contains purified recombinant AcrV-His protein as a control.

The expression of AcrV in *A. salmonicida* strain JF2267 was assessed by immunoblots using AcrV-His antibodies. When *A. salmonicida* was grown under standard culture conditions in TSB medium, no AcrV protein could be detected from total cells nor from culture supernatant of strain JF 2267, nor in the control of strains JF2397 and ATCC33658$^T$. However, when the cells are submitted to a low $Ca^{2+}$ response by chelating free $Ca^{2+}$ ions in the growth medium by the addition of 10 mM NTA, we detected AcrV with anti-AcrV antibodies in the pellet of JF2267 as a protein of about 37 kDa (FIG. 5) but not in strains JF2397 and ATCC33658$^T$, which are both devoid of the AcrV gene (FIG. 5). No AcrV protein could be detected in the supernatants of cultures from strains JF2267, JF2397 and ATCC33658$^T$, grown in $Ca^{2+}$ depleted medium.

When strain JF2267 was grown under standard culture conditions (containing free $Ca^{2+}$ ions) and then put in contact with RTG-2 cells at a ratio 2:1 (bacteria:cells) for 30 minutes, the AcrV protein could be monitored on immunoblots reacting with anti-AcrV, similar to cultures from $Ca^{2+}$ depleted medium.

Recombinant AcrV Vaccine Trial

Materials

Vaccine Formulations:

1. The AcrV vaccine was formulated using recombinant, Histidine-tagged AcrV resuspended in 10 mM phosphate buffer, pH 7.0, to 112.5 μg/mL. Four parts of this protein solution were mixed with one part oil adjuvant for a final AcrV concentration of 90 μg/mL. The dose for testing was 0.1 mL, or 9 μg/fish.

2. The commercial comparator vaccine was serial 4-13 of the vaccine MultiVacc4 (Bayotek International Ltd.)

3. The placebo (control) vaccine consisted of phosphate buffered saline (PBS) (10 mM phosphate, 150 mM NaCl, pH 7.2).

4. All vaccines were maintained at 4° C. until use.

Methods

Trial Design:

Fish (rainbow trout *Oncorhynchus mykiss*) that have been determined to be pathogen free and are at least 15 g in size are held for at least one-week pre vaccination for acclimation purposes. During the acclimation period the fish are offered 1% body weight in salmonid fish food every day, however they are denied food 24 hours pre and post-vaccination.

At least 50 fish are vaccinated 0.1 mL of AcrV vaccine via intra-peritoneal (IP) injection, or 0.2 mL of the commercial vaccine MultiVacc4. At the same time a group of at least 50 fish from the same stock are mock vaccinated with 0.1 mL of PBS. Vaccinated fish are then held for a period of at least 350-degree days to allow specific immune response generation in an acclimation tank with a continuous flow of water at a temperature of 12-13° C. The fish are offered 1% body weight in salmonid fish food daily until 24 hours pre-challenge and post-challenge.

After at least 350-dgree days post vaccination 50 fish per group were challenged by IP injection with a pre-determined concentration of virulent *Aeromonas salmonicida*. The dosage depends on the source of the fish and the water temperature (this is determined empirically immediately prior to challenge of test fish). The identical procedure is performed with the placebo vaccinated control fish. The fish are observed daily for mortality for 21 days post challenge and the cause of mortality assessed and examined to ensure that mortality is attributed to the challenge organism. After 24 hours post-challenge the fish are again offered 1% body weight in salmonid fish feed daily. Tanks are maintained with a continuous flow of water at a temperature of 12-13° C. For a challenge series to be considered satisfactory; all challenge groups must meet the following criteria:

1. At least 70% of the non-immunized controls must die within 21 days of challenge.
2. A relative percent survival (RPS) of no less than 25% must be achieved for the challenge disease before a vaccine is considered even partially efficacious for this disease.

RPS=[1−(% mortality vaccinates/% mortality controls)]×100

Developed from: The Rules Governing Medicinal Products in the European Union, Volume VII, Guidelines for the testing of veterinary medicinal products. 1994. Specific Requirements for the Production and Control of Live and Inactivated Vaccines Intended for Fish. Section 3.2. Potency.

Results

| Group | % Mortality | RPS |
|---|---|---|
| PBS | 82 | — |
| AcrV | 49 | 40 |
| MultiVacc4 | 30 | 63 |

There was a strong challenge with 82% control mortalities.

While particular elements, embodiments and applications of the present invention have been shown and described, it will be understood, of course, that the invention is not limited thereto, since modifications may be made by those skilled in the applicable technologies, particularly in light of the foregoing description. The appended claims include within their ambit such modifications and variants of the exemplary embodiments of the invention described herein as would be apparent to those skilled in the applicable technologies.

REFERENCES

Alschul, S. F., Gish, W., Miller, W., Myers, E. W. and Lipman, D. J.: Basic local alignment search tool. J. Mol. Biol. 215 (1990) 403-410.

Ausubel, F. M, Brent, R, Kingston, R. E., Moore, D. D., Seidman, J. G., Smith, J. A. and Struhl, K.: Current protocols in molecular biology. John Wiley & Sons, Inc., New York, N.Y., 1999.

Bairoch, A, Bucher, P. and Hofmann, K.: The PROSITE database, its status in 1995. Nucleic Acids Res. 24 (1995) 189-196.

Barve, S. S, and Straley, S. C.: lcrR, a low-$Ca^{2+}$ response locus with dual $Ca^{2+}$ dependent functions in *Yersinia pestis*. J. Bacteriol. 172 (1990) 4661-4671.

Bergman, T., Hakansson, S., Forsberg, A., Norlander, L. Macellaro, A., Backman, A., Bolin, I. and Wolf-Watz, H.: Analysis of the V antigen lcrGVH-yopBD operon of *Yersinia pseudotuberculosis*: evidence for a regulatory role of LcrH and LcrV. J. Bacteriol. 173 (1991) 1607-1616.

Birnboim, H. C. and Doly, J.: A rapid alkaline extraction procedure for screening recombinant plasmid DNA. Nucleic Acids Res. 7 (1979) 1513-1523.

Boland, A., Sory, M. P., Iriarte, M., Kerbourch, C., Wattiau, P. and Comelis, G. R.: Status of YopM and YopN in the *Yersinia* Yop virulon: YopM of *Y. enterocolitica* is internalized inside the cytosol of PU5-1.8 macrophages by the YopB, D, N delivery apparatus. EMBO J. 15 (1996) 5191-5201.

Braun, M., Kuhnert, P., Nicolet, J., Burnens, A. P. and Frey, J.: Cloning and characterization of two bistructual S-layer-RTX proteins from *Campylobacter rectus*. J. Bacteriol. 181 (1999) 2501-2506.

Bullock, W. O., Fernandez, J. M. and Short, J. M.: XL1-Blue: A high frequency efficiency plasmid transforming recA *Escherichia coli* strain with beta-galactosidase selection. Biotechniques 5 (1987) 376-378.

Cheng, L. W. and Schneewind, O.: *Yersinia enterocolitica* TyeA, an intracellular regulator of the type III machinery, is required for specific targeting of YopE, YopH, YopM, and YopN into the cytosol of eukaryotic cells. J. Bacteriol. 182 (2000) 3183-3190.

Chu, S., Cavaignac, S., Feutrier, J., Phipps, B. M., Kostrzynaska, M., Kay, W. W. and Trust, T. J.: Structure of the tetragonal surface virulence array protein and gene of *Aeromonas salmonicida*. J. Biol. Chem. 266 (1991) 15258-15265.

Cornelis, G. R.: The *Yersinia* Yop virulon, a bacterial system to subvert cells of the primary host defense. Folia Microbiol. (Praha) 43 (1998) 253-261.

Ellis, A. E: Immunization with bacterial antigens: furunculosis. Dev. Biol. Stand. 90 (1997) 107-116.

Fenselau, S., Balbo, I. and Bonas, U.: Determinants of pathogenicity in *Xanthomonas campestris* pv. *vesicatoria* are related to proteins involved in secretion in bacterial pathogens of animals. Mol. Plant Microbe Interact. 5 (1992) 390-396.

Fields, K. A. and Straley, S. C.: LcrV of *Yersinia pestis* enters infected eukaryotic cells by a virulence plasmid-independent mechanism. Infect. Immun. 67 (1999) 4801-4813.

Forsberg, A, Bolin, L, Norlander, L. and Wolf-Watz, H.: Molecular cloning and expression of calcium-regulated, plasmid-coded proteins of *Y. pseudotuberculosis*. Microb. Pathog. 2 (1987) 123-137.

Frank, D. W.: The exoenzyme S regulon of *Pseudomonas aeruginosa*. Mol. Microbiol. 26 (1997) 621-629.

Gill, S. C. and von Hippel, P. H.: Calculation of protein extinction coefficients from amino acid sequence data [published erratum appears in Anal Biochem 1990 September; 189(2):283]. Anal. Biochem. 182 (1989) 319-326.

Gough, C. L, Genin, S., Zischek, C. and Boucher, C. A.: hrp genes of *Pseudomonas solanacearum* are homologous to pathogenicity determinants of animal pathogenic bacteria and are conserved among plant pathogenic bacteria Mol. Plant Microbe Interact. 5 (1992) 384-389.

Harlow, E. and Lane, D.: Antibodies. A laboratory manual. Cold Spring Harbor Laboratory, 1988.

Hirono, L and Aoki, T.: Cloning and characterization of three hemolysin genes from *Aeromonas salmonicida*. Microb. Pathog. 15 (1993) 269-282.

Hofmann, K. and Stoffel, W.: TMbase—A database of membrane spanning proteins segments. Biol. Chem. Hoppe-Seyler 347 (1993) 166

Hueck, C. J.: Type III protein secretion systems in bacterial pathogens of animals and plants. Microbiol. Mol. Biol. Rev. 62 (1998) 379-433.

Iriarte, K and Cornelis, G. R.: Identification of SycN, YscX, and YscY, three new elements of the *Yersinia* yop virulon. J. Bacteriol. 181 (1999) 675-680.

Laemmli, U. K.: Cleavage of structural proteins during the assembly of the head of bacteriophage T4. Nature 227 (1970) 680-685.

Leary, S. E., Williamson, E. D., Griffin, K. F., Russell. P., Eley, S. M. and Titball, R. W.: Active immunization with recombinant V antigen from *Yersinia pestis* protects mice against plague. Infect. Immun. 63 (1995) 2854-2858.

Lee, K. K. and Ellis, A. E.: Glycemphospholipid:cholesterol acyltransferase complexed with lipopolysaccharide (LPS) is a major lethal exotoxin and cytolysin of *Aeromonas salmonicida*: LPS stabilizes and enhances toxicity of the enzyme. J. Bacteriol. 172 (1990) 5382-5393.

Lupas, A., Van, D. M. and Stock, J.: Predicting coiled coils from protein sequences. Science 252 (1991) 1162-1164.

Michiels, T. and Cornelis, G. R.: Secretion of hybrid proteins by the *Yersinia* Yop export system. J. Bacteriol. 173 (1991) 1677-1685.

Motin, V. L., Nakajima, R, Smirnov, G. B. and Brubaker, R. R.: Passive immunity to yersiniae mediated by anti-recombinant V antigen and protein A-V antigen fusion peptide. Infect. Immun. 62 (1994) 4192-4201.

Munro, A. L. and Hastings, T. S.: Furunculosis. In Inglis, V., Roberts, R. J. and Bromage, N. R. (Eds.), Bacterial diseases of fish. Blackwell Scientific, Oxford, 1993, pp. 122-142.

Nilles, M. L., Fields, K. A. and Straley, S. C.: The V antigen of *Yersinia pestis* regulates Yop vectorial targeting as well as Yop secretion though effects on YopB and LcrG. J. Bacteriol. 180 (1998) 3410-3420.

Nilles, M. L., Williams, A. W., Skrzypek, E. and Straley, S. C.: *Yersinia pestis* LcrV forms a stable complex with LcrG and may have a secretion-related regulatory role in the low-$Ca^{2+}$ response. J. Bacteriol. 179 (1997) 1307-1316.

Pettersson, J., Holmstrom, A., Hill, J., Leary, S., Frithz-Lindsten, E., Von Euler-Matell, A., Carlsson, E., Titball, R., Forsberg, A. and Wolf-Watz, H.: The V-antigen of *yersinia* is surface exposed before target cell contact and involved in virulence protein translocation. Mol. Microbiol. 32 (1999) 961-976.

Pitcher, D. G., Saunders, N. A. and Owen, R. J.: Rapid extraction of bacterial genomic DNA with guanidium thiocyanate. Lett. Appl. Microbiol. 8 (1989) 151-156.

Plano, G. V., Barve, S. S. and Straley, S. C.: LcrD, a membrane-bound regulator of the *Yersinia pestis* low-calcium response. J. Bacteriol. 173 (1991) 7293-7303.

Price, S. B. and Straley, S. C.: lcrH, a gene necessary for virulence of *Yersinia pestis* and for the normal response of *Y. pestis* to ATP and calcium. Infect. Immun. 57 (1989) 1491-1498.

Sawa, T., Yahr, T. L., Ohara, M., Kurahashi, K., Gropper, M. A., Wiener-Kronish, J. P. and Frank, D. W.: Active and passive immunization with the *Pseudomonas* V antigen protects against type III intoxication and lung injury [see comments]. Nat. Med 5 (1999) 392-398.

Schaller, A., Kuhn, R., Kuhnert, P., Nicolet, J., Anderson, T. J., MacInnes, J. L, Segers, R. P. A. M. and Frey, J.: Characterization of apxIVA, a new RTX determinant of *Actinobacillus pleuropneumoniae*. Microbiology 145 (1999) 2105-2116.

Skrzypek, E. and Straley, S. C.: LcrG, a secreted protein involved in negative regulation of the low-calcium response in *Yersinia pestis*. J. Bacteriol. 175 (1993) 3520-3528.

Studier, F. W., Rosenberg, A. H., Dunn, J. J. and Dubendorff, J. W.: Use of T7 RNA polymerase to direct expression of cloned genes. Methods Enzymol. 185 (1990) 60-89.

Thornton, J. C., Garduno, R. A., Carlos, S. J. and Kay, W. W.: Novel antigens expressed by *Aeromonas salmonicida* grown in vivo. Infect. Immun. 61 (1993) 4582-4589.

Titball, R. W. and Munn, C. B.: The purification and some properties of H-lysin from *Aeromonas salmonicida*. J. Gen. Microbiol. 131 (1985) 1603-1609.

Whitby, P. W., Landon, M. and Coleman, G.: The cloning and nucleotide sequence of the serine protease gene (aspA) of *Aeromonas salmonicida* ssp. salmonicida. FEMS Microbiol. Lett. 78 (1992) 65-71.

Yahr, T. L, Goranson, J. and Frank, D. W.: Exoenzyme S of *Pseudomonas aeruginosa* is secreted by a type III pathway. Mol. Microbiol. 22 (1996) 991-1003.

Yahr, T. L., Mende-Mueller, L. M., Friese, M. B. and Frank, D. W.: Identification of type III secreted products of the *Pseudomonas aeruginosa* exoenzyme S regulon. J. Bacteriol. 179 (1997b) 7165-7168.

Yahr, T. L, Mende-Mueller, L. M., Friese, M. B. and Frank, D. W.: Identification of type III secreted products of the *Pseudomonas aeruginosa* exoenzyme S regulon. J. Bacteriol. 179 (1997a) 7165-7168.

What is claimed is:

1. An isolated polynucleotide molecule encoding a polypeptide comprising an amino acid sequence selected from the group consisting of SEQ ID NO:1; SEQ ID NO:2; SEQ ID NO:3; SEQ ID NO:4; SEQ ID NO: 5; SEQ ID-NO:6; SEQ ID NO: 7; SEQ ID NO:8; and SEQ ID NO:9, or a complement thereof.

2. A plasmid comprising the isolated polynucleotide molecule of claim 1.

3. The plasmid of claim 2, wherein said plasmid is an expression vector.

4. An immunogenic composition comprising the expression vector of claim 3, and a pharmaceutically acceptable carrier.

5. An isolated polynucleotide comprising the nucleotide sequence of SEQ ID NO:10, or a complement thereof.

6. A plasmid comprising the isolated polynucleotide molecule of claim 5.

7. The plasmid of claim 6, wherein said plasmid is an expression vector.

8. An immunogenic composition comprising the expression vector of claim 7, and a pharmaceutically acceptable carrier.

* * * * *

SEQUENCE LISTING

<160> NUMBER OF SEQ ID NOS: 15

<210> SEQ ID NO 1
<211> LENGTH: 47
<212> TYPE: PRT
<213> ORGANISM: Aeromonas salmonicida

<400> SEQUENCE: 1

```
Glu Leu Lys Arg Leu Ile Arg Leu Leu Pro Val Glu Leu Phe Ser Glu
1               5                   10                  15
```

-continued

```
Glu Glu Gln Arg Gln Asn Leu Leu Gln Cys Cys Gln Gly Ala Leu Asp
            20                  25                  30

Asn Ala Ile Glu Arg Glu Glu Asp Glu Leu Ser Gly Glu Ser Ser
        35                  40                  45


<210> SEQ ID NO 2
<211> LENGTH: 123
<212> TYPE: PRT
<213> ORGANISM: Aeromonas salmonicida

<400> SEQUENCE: 2

Met Asn Trp Ile Glu Pro Leu Leu Val Gln Phe Cys Gln Asp Leu Gly
1               5                   10                  15

Ile Thr Ile Gly Asp Asn Pro His Ser Leu Ile Gln Leu Glu Leu Glu
            20                  25                  30

Gln Ser Gly Thr Leu Gln Leu Glu Arg His Gln Gly Gln Leu Thr Leu
        35                  40                  45

Trp Leu Ala Arg Ala Val Pro Trp His Gln Ser Gly Glu Ala Ile Arg
    50                  55                  60

Arg Ala Met Thr Leu Thr Ala Ala Ala Gln Gly Pro Ala Leu Pro Val
65                  70                  75                  80

Arg Ser Gly Trp Leu Gly Glu Glu Gln Leu Ile Leu Phe Val Ser Leu
                85                  90                  95

Asp Glu Arg Ala Val Thr Leu Pro Gln Leu His Gln Ala Val Thr Thr
            100                 105                 110

Leu Thr Arg Leu Gln Arg Glu Val Leu Ala Ser
        115                 120


<210> SEQ ID NO 3
<211> LENGTH: 121
<212> TYPE: PRT
<213> ORGANISM: Aeromonas salmonicida

<400> SEQUENCE: 3

Met Ser Arg Ile Thr Ala Ala His Ile Gly Ile Glu Gln Leu Ser Ala
1               5                   10                  15

Ile Ser Leu Asp Asp Gln Glu Arg Ser Leu Pro Gly Arg Tyr Ala Leu
            20                  25                  30

Leu Pro Asp Gly Gln Ser Ile Glu Pro His Ile Ser Arg Leu Tyr Pro
        35                  40                  45

Glu Arg Leu Ala Asp Arg Val Leu Leu Asp Phe Ala Thr Pro Asp Arg
    50                  55                  60

Gly Phe His Asp Leu Leu Arg Pro Val Asp Phe Asn Gln Ala Met Gln
65                  70                  75                  80

Gly Leu Arg Ser Val Leu Ala Glu Gly Gln Ser Pro Glu Leu Arg Ala
                85                  90                  95

Ala Ala Ala Leu Leu Glu Gln Met His Ala Asp Glu Gln Leu Met Gln
            100                 105                 110

Met Thr Leu His Leu Leu His Lys Val
        115                 120


<210> SEQ ID NO 4
<211> LENGTH: 116
<212> TYPE: PRT
<213> ORGANISM: Aeromonas salmonicida

<400> SEQUENCE: 4
```

-continued

Met Thr Met Val Leu Thr Ser Gln Gln Gln Asp Ala Leu Leu Leu Thr
1 5 10 15

Gly Trp Leu Gln Leu Gln Tyr Gly His Pro Asp Lys Ala Ser Val Leu
20 25 30

Leu Ala Ala Leu Leu Gln Ile His Pro Asp His Gln Gly Gly Arg Arg
35 40 45

Thr Leu Leu Val Ala Leu Leu Lys Gln Gly Glu Gly Glu Ala Ala Leu
50 55 60

Ala His Val Asp Gln Leu Met Gln Gln Gly Glu Ala Asp Gly Pro Leu
65 70 75 80

Trp Leu Cys Arg Ser Arg Ala Cys Gln Leu Ala Gly Arg Leu Asp Glu
85 90 95

Ala Arg Phe Ala Tyr Gln Gln Tyr Leu Glu Leu Glu Glu Gln Asn Glu
100 105 110

Ser Thr His Pro
115

<210> SEQ ID NO 5
<211> LENGTH: 116
<212> TYPE: PRT
<213> ORGANISM: Aeromonas salmonicida

<400> SEQUENCE: 5

Met Thr Met Val Leu Thr Ser Gln Gln Gln Asp Ala Leu Leu Leu Thr
1 5 10 15

Gly Trp Leu Gln Leu Gln Tyr Gly His Pro Asp Lys Ala Ser Val Leu
20 25 30

Leu Ala Ala Leu Leu Gln Ile His Pro Asp His Gln Gly Gly Arg Arg
35 40 45

Thr Leu Leu Val Ala Leu Leu Lys Gln Gly Glu Gly Glu Ala Ala Leu
50 55 60

Ala His Val Asp Gln Leu Met Gln Gln Gly Glu Ala Asp Gly Pro Leu
65 70 75 80

Trp Leu Cys Arg Ser Arg Ala Cys Gln Leu Ala Gly Arg Leu Asp Glu
85 90 95

Ala Arg Phe Ala Tyr Gln Gln Tyr Leu Glu Leu Glu Glu Gln Asn Glu
100 105 110

Ser Thr His Pro
115

<210> SEQ ID NO 6
<211> LENGTH: 93
<212> TYPE: PRT
<213> ORGANISM: Aeromonas salmonicida

<400> SEQUENCE: 6

Met Leu Val Arg Arg Glu Gly Glu Arg Ala Gly Leu Ala Asn Pro Phe
1 5 10 15

Ala Ala Leu Tyr Leu Leu Ala Glu Ala Thr Leu Ala Val Leu Gly Pro
20 25 30

Gly His Phe Leu Tyr Gly Asn Val Asp Val Phe Arg Ser Ser Ser Leu
35 40 45

Ser Ser Glu Arg Leu Gly Arg Phe Tyr Leu Arg Trp Thr Gly Ala Ser
50 55 60

Glu Pro Glu Pro Gly Trp Phe Met Leu Ala Thr Glu Gln Val Cys Ser
65 70 75 80

-continued

```
Leu Arg Asp Met Arg Lys Arg Gln Lys His Gly Leu Ala
                85                  90


<210> SEQ ID NO 7
<211> LENGTH: 94
<212> TYPE: PRT
<213> ORGANISM: Aeromonas salmonicida

<400> SEQUENCE: 7

Met Lys Gln Pro Arg Phe Ala Asp His Ser Glu Thr Ile Ser Gln Ala
1               5                   10                  15

Glu His Gly Ile Ala Asp Ser Asp His Arg Asn Ala Leu Leu Gln Glu
            20                  25                  30

Met Leu Ala Gly Leu Ala Leu Ser Asp Gln Thr Cys Gln Leu Leu Phe
        35                  40                  45

Glu Ala Pro Thr Glu Gln Val Ala Val Ala Glu Gln Glu Leu Leu Ala
    50                  55                  60

Glu Ile Gln Arg Arg Gln Ala Leu Leu Pro Ala Gln Pro Gly Glu Gly
65                  70                  75                  80

Arg Lys Ser Arg Arg Pro Thr Ile Met Arg Gly Leu Met Ile
                85                  90


<210> SEQ ID NO 8
<211> LENGTH: 361
<212> TYPE: PRT
<213> ORGANISM: Aeromonas salmonicida

<400> SEQUENCE: 8

Met Ser Thr Ile Pro Asp Tyr Asn Thr Asn Pro Gly Ala Phe Val Gly
1               5                   10                  15

Trp Leu Asp Val Gln Ala Leu Asn Thr Leu Pro Gly Asn Lys Asn Pro
            20                  25                  30

Lys Leu Thr Glu Leu Val Glu Leu Leu Lys Gly Lys Ile Thr Ile Ser
        35                  40                  45

Ala Asp Ser Ser Thr Ala Leu Ser Lys Glu Gln Leu Glu Lys Leu Leu
    50                  55                  60

Ala Ala Tyr Leu Thr Asp Pro Ala Ser Ile Asn Gly Gly Trp Ala Met
65                  70                  75                  80

Gly Gln Phe Lys Gly Gly Gln Asp Ala Ala Ile Ala Ala Ile Lys Gly
                85                  90                  95

Val Ile Glu Arg Gly Ala Lys Gln Thr Pro Pro Val Thr His Trp Thr
            100                 105                 110

Ile Pro Glu Phe Met Leu Leu Ser Leu Ser Ala Leu Thr Met Glu Arg
        115                 120                 125

Thr Asp Asp Asp Leu Ile Thr Thr Phe Thr Gly Val Met Met Phe Gln
    130                 135                 140

Asp Asn Gln Arg Lys Gly Leu Arg Asp Glu Leu Ala Glu Met Thr Ala
145                 150                 155                 160

Glu Leu Lys Ile Tyr Gly Val Ile Gln Ser Glu Ile Asn Gln Val Leu
                165                 170                 175

Ser Ala Ala Ser Asn Gln Thr Phe Lys Thr Asn Phe Asn Leu Met Asp
            180                 185                 190

Tyr Lys Leu Tyr Gly Tyr Glu Ser Leu Ala Lys Phe Met Glu Gly Gly
        195                 200                 205

Glu Phe Lys Leu Leu Ser Lys Met Phe Ser Asp Glu Gln Val Thr Lys
    210                 215                 220
```

-continued

```
Ala Gln Gln Asp Phe Thr Asn Ala Lys Asn Glu Leu Glu Asn Val Thr
225                 230                 235                 240

Ser Thr Ser Leu Asn Pro Lys Ile Gln Ala Glu Ala Lys Thr Asp Tyr
                245                 250                 255

Glu Arg Lys Lys Ala Ile Phe Glu Glu Ile Val Glu Thr Gln Ile Ile
            260                 265                 270

Thr Leu Lys Thr Phe Leu Glu Ser Asp Leu Lys Lys Ser Gly Ala Met
        275                 280                 285

Ser Gly Ile Glu Ala Glu Tyr Lys Tyr Asp Lys Asp Asn Asn Lys Leu
    290                 295                 300

Gly Asn Phe Ser Thr Ser Val Ser Asp Arg Ser Arg Pro Leu Asn Asp
305                 310                 315                 320

Leu Val Ser Glu Lys Thr Ala Arg Leu Asn Asp Val Ser Ser Arg Tyr
                325                 330                 335

Asn Ala Ala Ile Glu Ala Leu Asn Arg Phe Ile Gln Lys Tyr Asp Ser
            340                 345                 350

Ile Met Arg Asp Ile Leu Gly Ala Ile
        355                 360


<210> SEQ ID NO 9
<211> LENGTH: 159
<212> TYPE: PRT
<213> ORGANISM: Aeromonas salmonicida

<400> SEQUENCE: 9

Met Gln Thr Asp Thr Thr Leu Thr Pro Glu Tyr Glu Ala Glu Leu Glu
1               5                   10                  15

Ala Phe Met Ala Asp Gly Gly Thr Leu Ala Met Leu Gln Asp Ile Ser
            20                  25                  30

Gly Asp Thr Leu Glu Gln Leu Tyr Ala Leu Ala Phe Ser Gln Tyr Gln
        35                  40                  45

Ala Gly Lys Trp Glu Asp Ala His Lys Ile Phe Gln Ala Leu Cys Met
    50                  55                  60

Leu Asp His Tyr Glu Pro Arg Tyr Phe Leu Gly Leu Gly Ala Cys Arg
65                  70                  75                  80

Gln Ala Met Gly Glu Phe Glu Thr Ala Val Gln Ser Tyr Ser Phe Gly
                85                  90                  95

Ala Met Leu Asp Leu Lys Asp Pro Arg Phe Pro Phe His Ala Gly Glu
            100                 105                 110

Cys Arg Leu Gln Gln Gly Asp Leu Asn Gly Ala Glu Ser Gly Phe His
        115                 120                 125

Ser Ala Arg Leu Leu Ala Asp Thr Asp Pro Gln Gln Ala Asp Leu Ala
    130                 135                 140

Ala Ser Ala Lys Val Met Leu Glu Ala Ile Ala Ile Arg Arg Asp
145                 150                 155


<210> SEQ ID NO 10
<211> LENGTH: 5678
<212> TYPE: DNA
<213> ORGANISM: Aeromonas salmonicida

<400> SEQUENCE: 10

gagctcaagc ggctgatccg cctgctgccg gtggagctgt tcagtgaaga ggagcagcgc      60

cagaatctgt tgcagtgctg tcagggtgcg ctcgataacg ccatcgagcg ggaagaggat     120

gagttgtctg gagagtcgtc atgaactgga ttgaacccct gctggtgcag ttttgccagg     180
```

-continued

```
atttgggcat caccataggg gataaccccc attcgctgat ccagcttgaa ctggagcaga    240
gcggcactct gcagctggag cgccatcagg ggcaactgac cctatggttg gcccgcgccg    300
tgccctggca tcagagtggc gaggccattc gccgcgccat gaccttgact gccgcggcgc    360
aagggccggc actgccggtg cgcagcggct ggttggggga ggagcagttg atcctcttcg    420
tctccctgga tgagcgggcc gtgactctgc cccagctcca tcaggccgtg accaccctga    480
cccggttgca gcgagaggtg ctggcgtcat gagccggatc actgccgcgc atatcggtat    540
cgagcagctc agcgccatct ccctcgacga tcaggagcgc agcctgccgg ggcgttatgc    600
cctgttgccc gatggccagt ccatcgaacc ccatatcagc cgcctctacc ccgagcggct    660
ggcggatcgg gtgctgctcg atttcgccac cccggatcgc ggctttcacg acttgctgcg    720
accggtcgat ttcaatcagg cgatgcaggg gctgcgcagt gtgctggcag aggggcagag    780
ccccgaattg cgagcggccg ccgcgctgct cgaacaaatg cacgccgatg aacaactgat    840
gcagatgacc cttcatctgc tgcacaaggt atgaccatgg tgcttacgtc acagcagcag    900
gatgcgctgc tgctcaccgg ctggttgcaa ctgcaatatg gccaccctga caaggcgagc    960
gtgctgctgg ccgccctgct gcagatccac cccgaccatc agggagggcg acggaccttg   1020
ctggtggccc tgctcaaaca gggggagggg gaggcggcgc tggcccatgt cgatcagctg   1080
atgcagcaag gggaggccga cggcccgctc tggctctgtc gcagccgagc ctgccagttg   1140
gcagggcggc tggatgaagc ccgttttgcc tatcaacaat acctcgaact ggaagagcag   1200
aatgaatcaa cgcacccttg agttgctgcg ccggataggc gaacgcaagg acatcatgct   1260
ggcgatcctg ctgctggcca tcgtctttat gatggtcttg ccgctgccgc cggtggccct   1320
cgatatcctg attgccatca acatgaccat ctcggtggta ctgctgatga tggcggttta   1380
tatcaattcg ccgctgcagt tctccgcctt tccggcggtg ctgctgatca ccaccctgtt   1440
ccggcttgcc ttgtcggtga gtaccacccg gatgatcctg ctgcaggctg atgcggggca   1500
gatagtctac accttcggca acttcgtggt ggggggcaat ctggtggtgg ggatcgtcat   1560
cttcctcatc atcaccatcg tccagtttct ggtgatcacc aagggctcgg agcgggtcgc   1620
cgaggtgagc gcccgctttt ccctcgatgc catgccgggt aagcagatga gtatcgatgg   1680
tgacatgcgc gccggggtga tcgacgtgca cgaggcgcgg gatcgccgcg ggtcatcga    1740
gaaggagagc cagatgttcg gctccatgga tggcgccatg aagtttgtga agggggacgc   1800
catcgcgggc ctcatcatca tcttcgtcaa catcctcggt ggcgtcacca tcggggtgac   1860
ccagaagggg ttatccgccg ccgatgcgct gcagctctac tccatcctga cggtgggtga   1920
tggcatggtc tcccaggtgc cggcgctgct gatcgccatc accgcgggca ttatcgtcac   1980
ccgggtctcc tccgaagagt cttccgatct gggtaccgat atcggcgccc aggtggtggc   2040
ccagcccaag gcgctactga tcggcggtct gctgctggtg ctgttcgggt tgatcccggg   2100
cttcccgatg atcaccttct ttgcgctgtc ggccatcgtc acggcgggcg gttactttat   2160
cggcttgcga caacgcaagg cgcaaagcag caacagtcag gatcttcctg ccgtgctggc   2220
gcagggggcc ggggccccag ctgcccgcag caagccaaaa ccgggcagca agccgcgggg   2280
caagctgggg gagaaggagg agtttgccat gacggtgccg ctccttatcg atgtggatgc   2340
tgctttgcag gccgagctgg aggcgattgc cctcaacgac gaactggtgc gggtgcgccg   2400
cgccctctat ctcgatctcg ggtgcctttt cccgggtatt cacctgcgtt tcaacgaggg   2460
gatggggcct ggcgaatacc tgatccagct gcaggaggtg ccggtcgccc gcggtctgct   2520
gcgcccgggc catcagctgg tgcaggagag cgcctcccag ctcgatctgc tggggatccc   2580
```

-continued

```
ctacgaagag ggggcgccgt tactgccggg acaaccgacc ttgtgggtcg ctaatgaaca   2640
tcaggagcga ctggagaagt cacggctggc caccctcacc accgatcagg tgatgacctg   2700
gcatctatcc catgtgctgc gggaatatgc cgaggacttt atcggcattc aggagacccg   2760
ctacctgctg gagcagatgg aggggagcta tagcgagctg gtgaaggagg cgcaacgcat   2820
catcccgctg cagcgtatga ccgaaatttt gcagcggctg gtgggggagg atatctccat   2880
ccgcaacatg cgcgccatcc tcgaggcgat ggtggagtgg ggccagaagg agaaggatgt   2940
ggtgcagctc accgagtaca tccgtagcag cctcaagcgc tacatctgct acaagtacgc   3000
caacggcaac aacattttgc ctgcctatct gctcgatcag caggtggagg agcagctccg   3060
cggcggcatt cgccagacta gtgccggcag ctatctggcg ctcgatccca ctattaccca   3120
gagcttcctc gatcaggtgc gccacaccgt cggtgatctg gcccagatgc agaacaaacc   3180
ggtgctcatt gtctccatgg atatccgccg ctatgtgcgc aagctcatcg agggggatta   3240
ccatgccctg ccggtgctct cctatcagga gctgacccag cagatcaata tccagcccct   3300
cgggagggtc tgcctgtgag gggggacccg ttaacctctg accccctgat cccctggctg   3360
caggccaagg gtgtggcggt tgcctctcac tatctggggg caacccccat ccagctcggc   3420
cacgctttct gctatcgcca aatttatctc gcctggcggg ttgatcctac gacccgacgg   3480
gtctggatca tgctggtgcg ccgagagggg gagcgggctg gactggccaa tccctttgcc   3540
gccctctatc tgctggccga agccactctg gctgtactcg gtccgggcca tttcctctac   3600
ggcaacgtcg atgtctttcg aagcagtagc ctgagcagtg agcggctagg ccgcttctac   3660
ttgcgctgga cgggagccag tgaacccgag cccggctggt tcatgttggc caccgagcaa   3720
gtctgttcac tacgggatat gcgaaaacga caaaagcacg gccttgcgtg acaggcatgt   3780
ccaaaagggc ctcatagaat aggagccaag atgaaacaac cgcgttttgc cgaccatagc   3840
gagaccattt cgcaggcaga gcatggcatt gccgacagcg atcaccgcaa tgccctgttg   3900
caagagatgc tggctggcct agccctctcg gatcagacct gtcagctgct gttcgaagcg   3960
ccgaccgagc aagtggccgt ggccgagcag gagttgttgg cagagatcca gcgcagacag   4020
gcgttactac cggcacagcc gggagagggc cgcaaaagtc gccgtcccac cattatgcgc   4080
ggactgatga tttaaggagt cgtgatgagc acaatccctg actacaacac taaccccggc   4140
gcgttcgtcg gctggcttga tgtgcaagca ctgaacacat tgccgggcaa taaaaatccc   4200
aagttgaccg aactggtcga gctgctcaag ggcaagatca ccatcagtgc tgactcatcg   4260
actgcgctga gcaaggagca gctggagaag ttgctggctg cctatctgac ggatcctgcc   4320
tcgatcaacg gggctgggc gatgggccag ttcaagggag gtcaagatgc cgccattgcc   4380
gccatcaagg gggtgatcga gcggggagca aaacaaaccc cgccagtcac ccactggacc   4440
atccctgaat ttatgctgct ctccctcagt gcgctgacca tggaacgtac cgatgacgat   4500
ctcatcacga cctttaccgg ggtgatgatg tttcaggaca atcagcgtaa agggttgcgg   4560
gatgagctgg cagagatgac cgctgagctg aagatctacg ggtgatcca gtccgagatc   4620
aaccaggtgc tctctgcggc gtccaaccaa accttcaaaa ccaatttcaa tctgatggat   4680
tacaagctct atggctatga gtctctggcc aaatttatgg aagggggcga gttcaagctg   4740
ttgtcaaaaa tgtttagcga tgagcaggtg acaaaagcac agcaagattt caccaatgct   4800
aaaaatgagc tggaaaacgt cacgtcgacc agcctaaacc ccaaaatcca ggcggaagct   4860
aagaccgatt atgagcgtaa aaaagccatt tttgaggaga tcgtagagac gcagatcatc   4920
```

-continued

```
acccttaaaa cgttcctgga aagtgacctg aagaagagcg gcgccatgag tggcatagaa   4980

gccgagtaca aatatgacaa agacaacaac aagcttggca acttctccac tagtgtgagc   5040

gaccgttctc gcccgctcaa cgatctggtc agtgaaaaga ccgcccgcct caacgacgtc   5100

agttcgcgct acaacgctgc catcgaggca ctcaaccgct ttatccagaa atacgacagc   5160

atcatgcgcg acattcttgg cgcaatttga ggagagatca tgcagaccga caccaccctg   5220

accccggaat atgaagcaga gctggaggcc tttatggctg acggtggtac cctggctatg   5280

ctgcaggata tctctggcga caccttggaa cagctctatg ccctggcctt tagccagtat   5340

caggccggca agtgggaaga tgctcacaaa atcttccagg ctctctgcat gctggatcac   5400

tacgagccac gctatttcct cgggctgggt gcttgccgtc aggcgatggg ggagtttgaa   5460

acggcagttc agagttacag ctttggcgcc atgctcgacc tgaaagatcc ccgtttccca   5520

tttcatgcag gcgagtgccg gctgcaacaa ggtgatttga acggtgccga gagtggcttc   5580

cactcggccc gactgctggc ggacacagat ccccagcagg cagacctggc ggcaagcgcc   5640

aaggtcatgt tggaagccat cgcaatcaga agggatcc                           5678


<210> SEQ ID NO 11
<211> LENGTH: 30
<212> TYPE: DNA
<213> ORGANISM: Artificial
<220> FEATURE:
<223> OTHER INFORMATION: Synthetic primer.

<400> SEQUENCE: 11

gggaattcga tgagcacaat ccctgactac                                      30


<210> SEQ ID NO 12
<211> LENGTH: 30
<212> TYPE: DNA
<213> ORGANISM: Artificial
<220> FEATURE:
<223> OTHER INFORMATION: Synthetic primer.

<400> SEQUENCE: 12

atgcggccgc aaattgcgcc aagaatgtcg                                      30


<210> SEQ ID NO 13
<211> LENGTH: 29
<212> TYPE: DNA
<213> ORGANISM: Artificial
<220> FEATURE:
<223> OTHER INFORMATION: Synthetic primer.

<400> SEQUENCE: 13

tcgcggccgc accctttacg ctgattgtc                                       29


<210> SEQ ID NO 14
<211> LENGTH: 28
<212> TYPE: DNA
<213> ORGANISM: Artificial
<220> FEATURE:
<223> OTHER INFORMATION: Synthetic primer.

<400> SEQUENCE: 14

cggaattcgt tgcgggatga gctggcag                                        28


<210> SEQ ID NO 15
<211> LENGTH: 30
<212> TYPE: DNA
<213> ORGANISM: Artificial
```

-continued

```
<220> FEATURE:
<223> OTHER INFORMATION: Synthetic primer

<400> SEQUENCE: 15

tcgcggccgc actcggcttc tatgccactc                                        30
```